United States Patent
Fisher et al.

(10) Patent No.: US 6,689,319 B1
(45) Date of Patent: Feb. 10, 2004

(54) APPARATUS FOR DEPOSITION AND INSPECTION OF CHEMICAL AND BIOLOGICAL FLUIDS

(75) Inventors: William D. Fisher, San Jose, CA (US); Henrique A. S. Martins, Cupertino, CA (US); Peter G. Webb, Menlo Park, CA (US)

(73) Assignee: Agilent Technologies, Ind., Palo Alto, CA (US)

( * ) Notice: Subject to any disclaimer, the term of this patent is extended or adjusted under 35 U.S.C. 154(b) by 0 days.

(21) Appl. No.: 09/429,895

(22) Filed: Oct. 29, 1999

(51) Int. Cl.[7] .............................................. G01N 35/10
(52) U.S. Cl. ........................ 422/67; 422/82.05; 422/100
(58) Field of Search .............................. 422/62–63, 67, 422/100, 82.05; 436/43, 49, 55, 180, 518; 435/287.2–287.3; 347/20, 106, 37; 356/394, 398; 250/559.07, 559.08, 559.29

(56) References Cited

U.S. PATENT DOCUMENTS

| | | | |
|---|---|---|---|
| 4,379,308 A | * 4/1983 | Kosmowski et al. | 348/126 |
| 4,495,149 A | * 1/1985 | Iwata et al. | 134/170 |
| 4,675,696 A | * 6/1987 | Suzuki | 346/46 |
| 4,877,745 A | 10/1989 | Hayes et al. | 436/166 |
| 4,929,845 A | * 5/1990 | Amir et al. | 250/559.05 |
| 5,338,688 A | 8/1994 | Deeg et al. | 436/180 |
| 5,384,859 A | * 1/1995 | Bolza-Schunemann et al. | 347/19 |
| 5,445,934 A | 8/1995 | Fodor et al. | 435/6 |
| 5,474,796 A | 12/1995 | Brennan | 427/2.13 |
| 5,508,200 A | 4/1996 | Tiffany et al. | |
| 5,601,980 A | 2/1997 | Gordon et al. | |
| 5,629,169 A | * 5/1997 | Izraelevitz et al. | 435/32 |
| 5,658,802 A | 8/1997 | Hayes et al. | 436/518 |
| 5,700,637 A | 12/1997 | Southern | 435/6 |
| 5,721,435 A | * 2/1998 | Troll | 250/559.29 |

(List continued on next page.)

FOREIGN PATENT DOCUMENTS

| | | | |
|---|---|---|---|
| EP | 0385625 A2 | 9/1990 | |
| EP | 0916396 A2 | 5/1999 | |
| EP | 1096250 A2 | 5/2001 | |
| GB | 2355716 | * 2/2001 | ............ B01J/19/00 |
| WO | WO 95/35505 | 12/1995 | ......... G01N/33/543 |
| WO | WO 9807022 A1 | * 2/1998 | .......... G01N/21/64 |
| WO | WO 00/06306 | 2/2000 | |
| WO | WO 00/60529 | 10/2000 | |

OTHER PUBLICATIONS http:/www.parkardisnt.com/prod_serv/biochiparrayer.htm, "BioChip Arrayer: Automated DNA Microarray Fabrication", Packard Instruments Company, date downloaded–Oct. 13, 1999.*
http:/www.parkardbioscience.com/products/products.asp-?content_item_id=331, "BioChip Arrayer: Your Solution for Automated DNA Microarray Fabrication", Packard Bio-Science Company, date downloaded–Feb. 8, 2002.*
Brochure—"BioChip Arrayer", Packard Instrument Company, 1999.

*Primary Examiner*—Jeffrey Snay

(57) ABSTRACT

An apparatus and method are provided for producing and inspecting a plurality of deposited features in a pattern on a portion of a substrate surface, as in an oligonucleotide array. The apparatus comprises a printhead for depositing a fluid to form the array of features on the substrate surface and a camera for imaging the deposited features. The apparatus also comprises a printhead controller for positioning and activating the inkjet printhead to deposit the array features. The camera, e.g., a digital line scan camera, is controlled by a camera controller such that the camera acquires images corresponding to substantially only the portion of the surface on which features should have been deposited. The camera and printhead are preferably situated such that an induced movement of the printhead relative to the substrate results in a substantially identical corresponding movement of the camera. Optionally, the apparatus further comprises means for comparing an image acquired by the camera with a predetermined standard to produce a signal.

25 Claims, 3 Drawing Sheets

U.S. PATENT DOCUMENTS

| | | | |
|---|---|---|---|
| 5,724,437 A | * 3/1998 | Bucher et al. | 101/183 |
| 5,807,522 A | 9/1998 | Brown et al. | 422/50 |
| 5,882,720 A | * 3/1999 | Legault et al. | 228/102 |
| 5,984,470 A | * 11/1999 | Sakino et al. | 347/106 |
| 6,151,040 A | * 11/2000 | Takada et al. | 347/106 |
| 6,232,072 B1 | * 5/2001 | Fisher | 435/6 |
| 6,323,043 B1 | * 11/2001 | Caren et al. | 346/140.1 |
| 6,447,836 B1 | 9/2002 | Schrof et al. | |

* cited by examiner

APPARATUS FOR DEPOSITION AND INSPECTION OF CHEMICAL AND BIOLOGICAL FLUIDS

TECHNICAL FIELD

This invention relates generally to devices used in fluid deposition and inspection and more particularly relates to an apparatus for depositing and selectively inspecting chemical and biological fluid arrays.

BACKGROUND

In the fields of chemistry, biochemistry, and molecular biology, there is a need to improve capabilities for carrying out large numbers of reactions using small quantities of materials in a short time period. As a result, there is a significant and growing interest in employing array technologies where the arrays comprise an ever increasing number of distinct features on a relatively small substrate.

Many methods for making arrays of biological materials are currently available. Generally, DNA arrays are fabricated on a solid substrate by deposition of whole DNA oligomers or complementary DNA or by in-situ synthesis of DNA oligomers. Specific methods for fabricating biological arrays are summarized in international patent publication WO 95/35505. This reference discusses the "dot blot" technique in which a vacuum manifold transfers a number of DNA samples from circular wells to a porous membrane. In addition, DNA sequences can also be synthesized by using a photolithographic technique as discussed in U.S. Pat. No. 5,445,934 to Fodor et al., and by using a capillary dispenser tapping technique as discussed in U.S. Pat. No. 5,807,522 to Brown et al. All of these techniques suffer from inherent limitations that reduce the capacity for producing arrays accurately and reliably.

Arrays may be prepared by a variety of methods employed in the printing industry that do not suffer from the aforementioned limitations. U.S. patent applications Ser. Nos. 09/150,504 and 09/150,507 describe forming biomolecular arrays by adaptations of devices employed in the printing industry and, particularly, of inkjet printheads and of automated devices for moving a printhead over a print surface and for depositing fluids at desired locations on the surface. Other uses of inkjet printing devices to dispense biochemical agents such as proteins and nucleic acids are suggested or described in, for example, U.S. Pat. Nos. 5,658,802; 5,338,688; 5,700,637; 5,474,796; 4,877,745; and 5,449,754. In essence, inkjet printing processing as applied to array fabrication involves feeding fluid composition from a reservoir into a dispensing chamber of an inkjet printhead and providing a stimulus repeatedly to cause the fluid composition to issue from a nozzle or orifice toward a substrate at desired locations, thus forming an array of features.

It is important to deposit uniform features, particularly when automated array fabrication techniques are used. In co-pending, commonly assigned U.S. patent application Ser. No. 09/150,504, filed Sep. 9, 1998, for "Method and Apparatus for Making Nucleic Acid Arrays" by Caren et al., an apparatus is described that can be used to deposit an array of uniform nucleic acid features on a substrate surface. The apparatus can form arrays by depositing droplets in the picoliter range on substrates having a rectangular surface of various sizes, 125 mm by 80 mm for example as described in the application, resulting in an enormous number of features deposited on a single substrate surface. In addition, after a feature is deposited, there is a need to inspect each feature of the array for characteristics such as size, shape, position and the like.

The use of digital video cameras for inspection of deposited materials on substrates is generally well known. U.S. Pat. No. 5,724,437 to Bucher et al., for example, describes a device for parallel image inspection and ink control on a printed product. In addition, camera-based inspection systems for arrays are widely known in the field of semiconductor processing. U.S. Pat. No. 5,882,720 to Legault et al. describes an inspection system that automatically monitors pads of materials deposited on a surface of a workpiece using an inspection system having charged couple device. U.S. Pat. No. 5,812,268 to Jackson et al. describes a grid array inspection system and method where the grid array is placed upon a fixture above a motion control table and scanned with a three-dimensional scanner. U.S. Pat. No. 4,929,845 to Amir et al. describes the use of a line scan camera to inspect a circuit board for proper placement of components to be soldered prior to soldering. In the biological field, U.S. Pat. No. 5,629,169 to Izraelevitz et al. describes a method of estimating effectiveness of antibiotics by analyzing the digital image of a plurality of antibiotic disks positioned a substrate containing a population of test organisms.

One possible way to inspect an array is to wait until after the entire array has been deposited, then digitize the image of the entire substrate, and finally process the data for each feature. However, as the number of features deposited in an array increases with improving technology, the amount of memory needed to store an entire array image becomes enormous. Generally, waiting for an array to be completed for imaging is an inefficient use of time. In certain cases, multiple deposition cycles or passes, i.e., the successive deposition of subarrays, are needed to deposit all the features in an array. In such cases, subarrays may be arranged in a manner such that a long time interval may pass before adjacent features are deposited. When the goal of inspection is to image the features immediately following or soon after deposition of liquid-containing features before the features are dry, multiple inspection cycles may be required to inspect features within a subarray with each inspection cycle or pass. Thus, there is a need to acquire and analyze images of deposited array features as features are being deposited.

SUMMARY OF THE INVENTION

Accordingly, it is an object of the present invention to overcome the above-mentioned disadvantages of the prior art by providing a new apparatus to deposit a pattern of features on a surface of a substrate and to acquire images of the features.

It is another object of the invention to provide such an apparatus to improve efficient use of time and computing resources in inspecting the features on a substrate by reducing the imaging data acquired for inspection of features in an array.

It is still another object of the invention to provide such an apparatus employing a line scan camera to acquire and inspect images of a pattern of features.

It is a further object of the invention to provide such an apparatus to deposit features in an array to allow for controlled activation of a camera to minimize the acquisition of unnecessary imaging data.

It is a further object of the invention to provide such a means for a computerized controller to active a camera based on reading of a image or data file.

It is still a further object of the invention to provide such an apparatus to inspect a pattern of features on a substrate while the pattern is being deposited.

It is another object of the invention to provide such an apparatus to detect deficiencies in array fabrication and to generate a signal to flag the deficiency.

It is still another object of the invention to provide such an apparatus to control the quality of features deposited on a substrate during automated array fabrication.

Additional objects, advantages and novel features of the invention will be set forth in part in the description which follows, and in part will become apparent to those skilled in the art upon examination of the following, or may be learned by practice of the invention.

In one aspect, then, the present invention relates to an apparatus for producing and inspecting a plurality of features in a pattern on a portion of a surface of a substrate. The apparatus comprises a printhead for depositing a fluid to form a plurality of features in a pattern on the surface of the substrate and an image acquisition system for imaging the deposited features. Also provided is a printhead controller for positioning and activating the inkjet printhead to deposit sequentially the plurality of features in the pattern. The image acquisition system comprises a camera controlled by a camera controller such that the camera acquires images corresponding to a first portion of the surface on which the features should have been deposited and less than all of a second portion of the surface that is nominally featureless. Preferably, the camera controller and printhead controller are coupled such that activation of the printhead by the printhead controller is accompanied with imaging by the camera. Corresponding imaging may or may not occur simultaneously. In addition, it is preferred that the camera and printhead are respectively situated such that an induced movement of the printhead relative to the substrate results in a substantially identical corresponding movement of the camera relative to the substrate.

In another aspect, the invention as described above further comprises means for comparing an image acquired by the camera with a predetermined standard to produce a signal. The signal can alert an operator of the apparatus of a defectively deposited feature so that experimental data derived from such features are discarded. Alternatively, the signal can trigger corrective action by the printhead controller to adjust deposition parameters accordingly, such that features remain within specified limits.

In a further aspect, the invention is directed to an apparatus for inspecting a plurality of features in a pattern on a portion of a surface of a substrate. The apparatus comprises a camera for imaging the surface of the substrate and a controller for positioning and activating the camera to acquire images corresponding to the portion of the surface on which the features have been deposited and less than all of the portion of the nominally featureless portion of the surface. The apparatus optionally comprises means for comparing an image acquired by the camera with a predetermined standard to produce a signal. The signal may be used to alert an operator of inadequately formed features.

BRIEF DESCRIPTION OF THE FIGURES

The invention is described in detail below with reference to the following drawings.

DETAILED DESCRIPTION OF THE INVENTION

Figure 1:
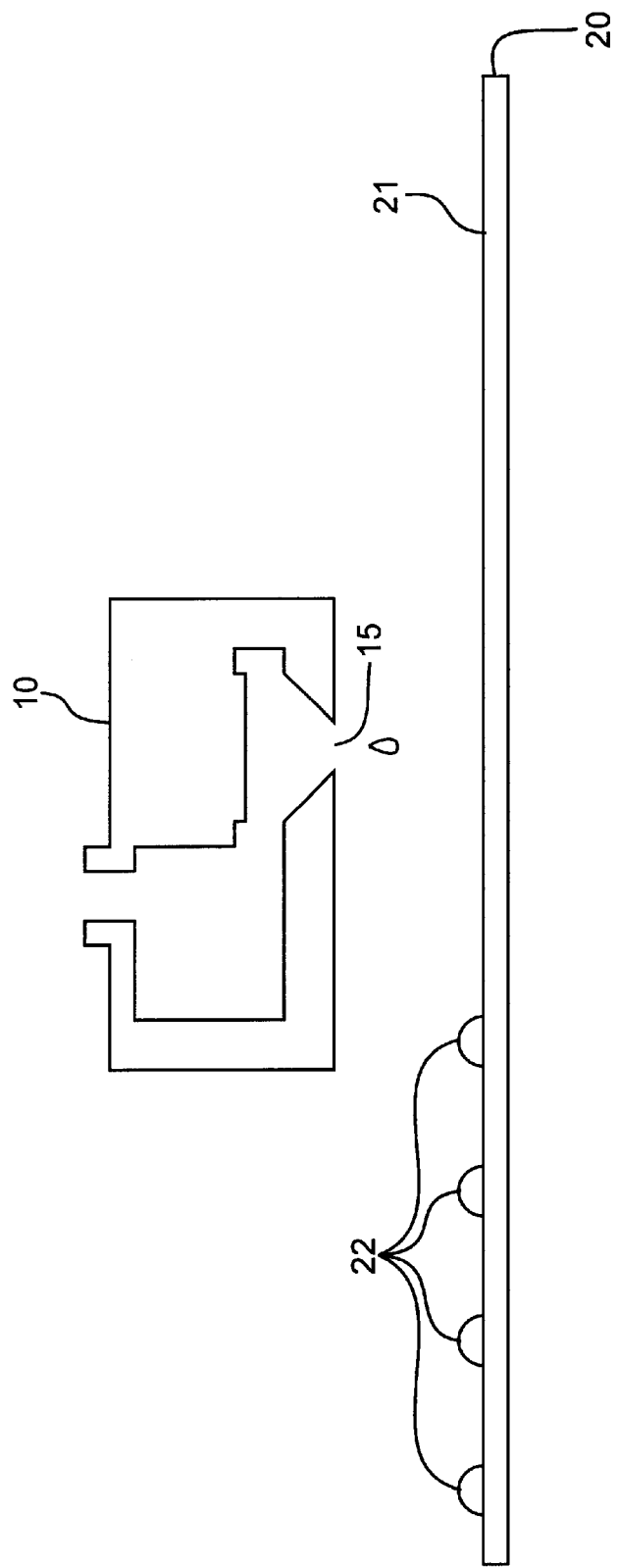
FIG. 1 schematically illustrates a cross-sectional side view of an inkjet printhead depositing a fluid through a dispensing orifice to form a plurality of features on a surface of a substrate.

Before describing the invention in detail, it must be noted that, as used in this specification and the appended claims, the singular forms "a," "an," and "the" include plural referents unless the context clearly dictates otherwise. Thus, for example, reference to "a feature" includes more than one feature, reference to "an image" includes a plurality of images, reference to "a light source" includes a plurality of light sources and the like.

In describing and claiming the present invention, the following terminology will be used in accordance with the definitions set out below.

The term "array" used herein refers to a regular, orderly, and two-dimensional pattern of features. Arrays typically but do not necessarily comprise at least 1,000 and preferably at least 100,000 features. An array differs from a pattern in that patterns are not necessarily regular and orderly.

The term "feature" refers to an element or a constituent part of matter forming a pattern situated on a surface. As used herein, features can be deposited, dispensed, printed, placed, positioned or otherwise disposed on a surface.

The term "nominal" used herein refers to a desired state that may vary from the actual state. For example, a "nominally" featureless portion of a surface refers to the portion of the surface on which no feature is supposed to be deposited. In addition, a "nominal" position of a feature on a surface is the position where a feature should be or should have been deposited.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the method of the invention. Examples of oligomers and polymers include polydeoxyribonucleotides, polyribonucleotides, other polynucleotides that are—or C-glycosides of a purine or pyrimidine base, polypeptides, polysaccharides, and other chemical entities that contain repeating units of like chemical structure. In the practice of the instant invention, oligomers generally comprise about 2–10000 monomers or more in certain instances.

The term "pattern" refers to a group or collection of sites on a surface on which features can be deposited. Each site has both a location and an area.

The present invention in general terms is directed to an apparatus for inspecting a plurality of features in a pattern on a surface of a substrate that preferably includes means for deposition of features. Unlike typical inspection devices that employ a camera to image an entire workpiece, the present invention employs a camera to image only portions of the surface of a substrate on which a feature should have been deposited. The inspection apparatus can be employed during or after the deposition of the features of the pattern. In addition, the preferred camera employed by the present invention is a line scan camera capable of producing digital data typically used in the inspection of continuous webs. Furthermore, the invention is particularly useful in conjunction with the automated production of biochemical arrays containing a large number of features using inkjet technology. Because large arrays, particularly those produced by multiple cycles of deposition, necessarily imply a large quantity of imaging data, imaging only portions of the substrate surface minimizes waste of memory and computational resources.

FIG. 1 schematically illustrates a cross-sectional side view of a printhead 10 depositing a pattern of features 22 on the surface 21 of a substrate 20. While many different types of printheads can be used in conjunction with the present invention, an inkjet printhead is shown. The dispensing orifice 15 of the printhead 10 is typically but not always oriented downward to deposit droplets of fluid onto the substrate 20. The pattern of features is formed by inducing a relative movement between the printhead 10 and substrate 20 such that the printhead passes over the substrate in a patternwise manner. It is not critical whether movement is induced in the printhead 10, substrate 20 or both for depositing a pattern of biomolecular fluid on the substrate 20. Typically, however, the printhead 10 is moved while the substrate 20 remains stationary. Whenever the dispensing orifice 15 of the printhead 10 is located directly above the substrate 20 where a feature 22 is desired, i.e., the nominal position of the feature, the printhead 10 is activated to deposit a droplet of fluid onto the substrate 20.

The typical printhead is controlled by a printhead controller that may be a combination of software, firmware and/or hardware. The printhead controller typically includes a position encoder and a motion controller. The position encoder measures the position of the printhead and generates a position signal. The motion controller moves the printhead. In the case of a closed-loop motion control system, the motion controller monitors the position signal to provide position error feedback control. In the case of an open-loop motion control system, the position signal is not monitored. The printhead controller keeps track of the position of the printhead by monitoring the position signal and decides whether to fire a dispenser at any particular position. If the printhead has more than one dispenser, the printhead controller must have a channel for each dispenser that is to be independently controlled. To decide whether to fire any dispenser, the controller references an image or data file that contains the information about what to fire at each location. If programmed with information regarding the relative locations of each dispenser, the controller can translate the image or data file into a dispenser position to determine when a dispenser is fired as the printhead is moved. A channel can also be set aside to independently control the activation of other devices such as an image acquisition system. In such a case, such a channel may comprise another controller. For example, if a device controller comprises seven channels, six of which are used to independently control six dispensers of a printhead and one is used to control a camera, the six channels used to control the dispensers would be considered part of one controller, i.e., the printhead controller, and the one channel used to independently control the camera would be considered part of another controller, i.e., the camera controller. If both the aforementioned controllers reference the same image or data file even though the controllers may otherwise independent of each other, the controllers are said to be coupled. Alternatively, the aforementioned device controller can be characterized as a printhead controller that also controls the camera.

Figure 2:
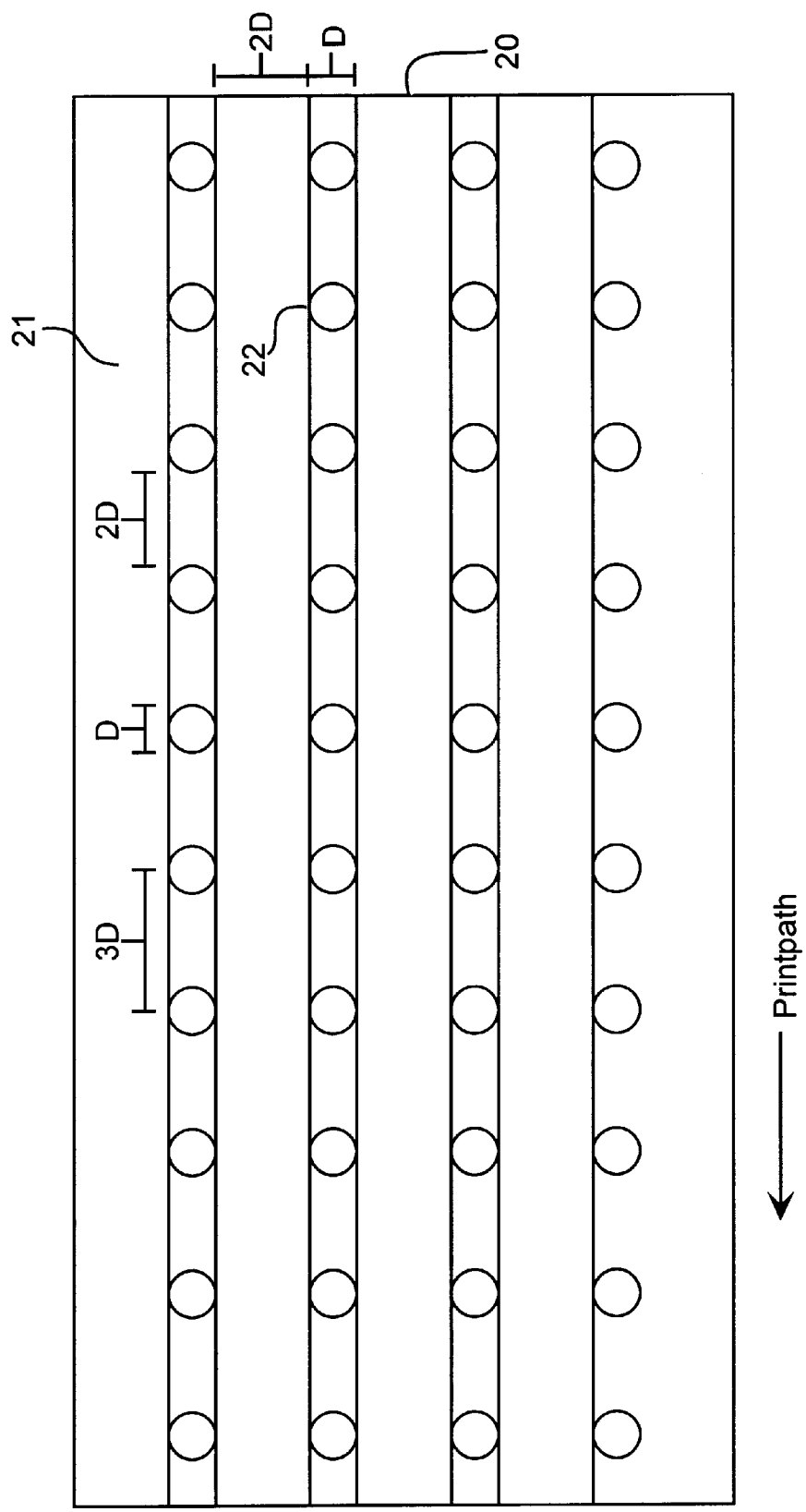
FIG. 2 schematically illustrates a top view of an array of features deposited on a surface of a rectangular substrate.

FIG. 2 schematically illustrates a top view of an array of features 22 deposited on a surface 21 of a rectangular substrate 20. An inkjet printer can deposit features in a variety of patterns. One pattern for biomolecular fluids is a square array where each feature 22 is equidistant from four other features as shown in FIG. 2. This arrangement provides for a simple geometry to facilitate automated array fabrication and inspection. Since many substrates employed in biomolecular arrays are rectangular in shape, this arrangement also provides for efficient use of substrate surface area. It is apparent from this illustration that the features are not contiguous but that the nominally featureless portion of the surface intervenes therebetween, i.e., the nominally featureless portion of the surface provides for spacing between individual features. Other possible patterns that provide for efficient use of substrate surface area include a close-pack hexagonal array where each feature in the array is equidistant from six other features on the same plane. Still other patterns are apparent to one of ordinary skill in the art. It is important to emphasize that not all features are necessarily deposited during a single motion of the printhead, i.e., a print pass. An array may be deposited through successive cycles in subarrays arranged in a manner such adjacent features are not necessarily deposited successively.

Figure 3:
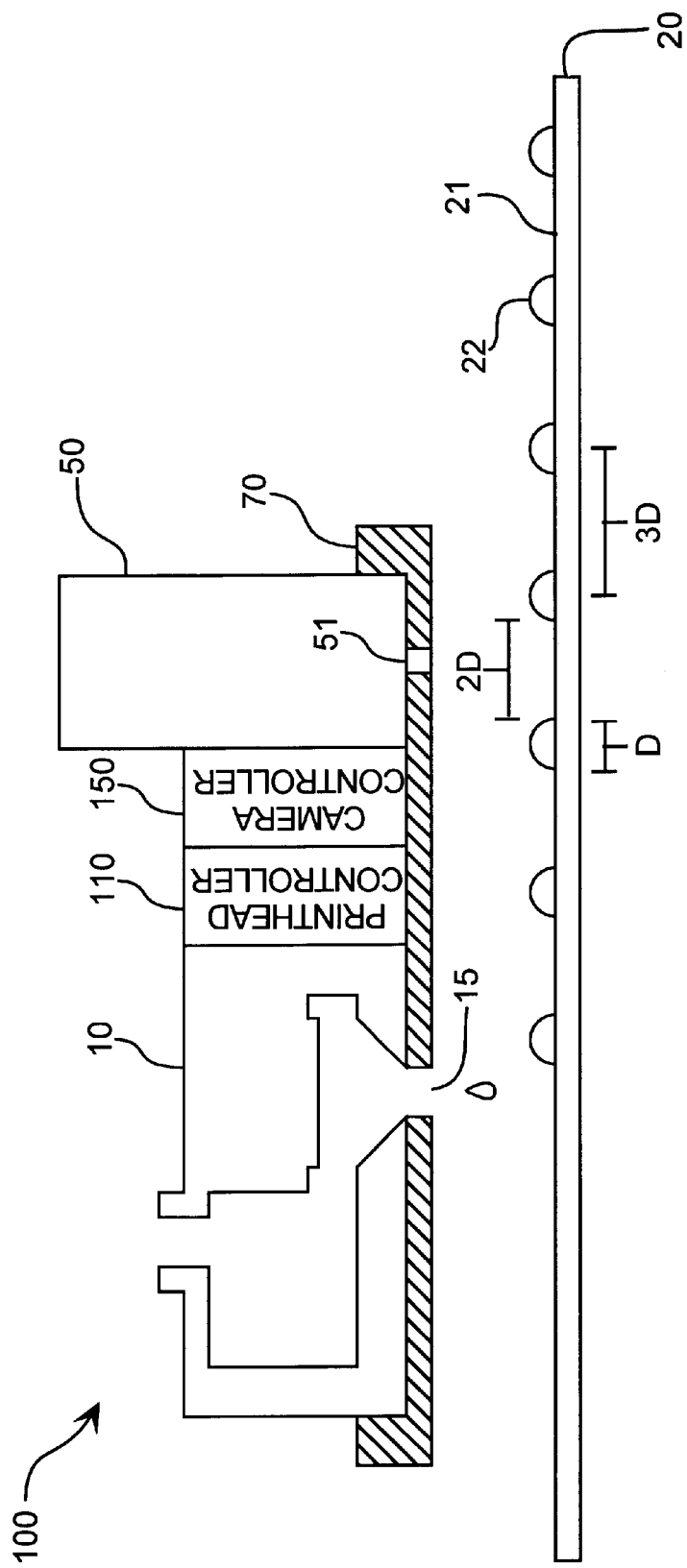
FIG. 3 schematically illustrates a cross-sectional side view of a preferred apparatus for producing and inspecting a plurality of features in a pattern on a surface of a substrate.

FIG. 3. schematically illustrates a cross-sectional side view of a preferred embodiment of the present invention. Apparatus 100 is used to produce and inspect a plurality of features 22 in a pattern on a surface 21 of a substrate 20. The apparatus 100 comprises an inkjet printhead 10 for depositing a fluid to a form a plurality of features 22 on substrate surface 21, and a camera 50 for imaging the substrate surface. Also provided are a printhead controller 110 for positioning and activating the inkjet printhead 10 to sequentially deposit the plurality of features 22 in the pattern and a camera controller 150 for controlling the camera 50 such that the camera images substantially only the portion of the surface on which a feature should have been deposited. Collectively, the camera 50 and the camera controller 150 are referred to as the image acquisition system. Other suitable image acquisition systems include the optical detection system set forth in U.S. Pat. No. 5,721,435 to Troll. Preferably, the camera controller 150 and the printhead controller 110 are coupled such that whenever the inkjet printhead 10 is activated by the printhead controller 110, the camera controller 150 is correspondingly triggered to activate the camera 50 to image a portion of the surface 21 on which a feature 22 should have been deposited.

Typically, the apparatus is designed such that the camera images only the smallest practicable portion of the nominally featureless surface, i.e., the surface on which no feature should have been deposited. Thus, substantially only the portion of the surface on which a feature should have been deposited is imaged. When multiple print passes are employed, the apparatus is designed such that the camera images only the smallest portion of the surface on which no feature should have been deposited during the particular print pass. As a consequence, each feature is imaged once, and duplicative imaging of features is minimized or at least lessened. It is desired that the camera images less than all of the nominally featureless portion of substrate surface. Preferably, no more than about 50 percent of the nominally featureless surface is imaged. More preferably, no more than about 25 percent of the nominally featureless surface is imaged. Still more preferably, no more than about 10 percent of the nominally featureless surface is imaged. To make a camera minimize imaging of a nominally featureless portion of a surface of a substrate, one can adjust the field of view of the camera such that the field of view corresponds to the nominal feature area. Then, the camera is activated only when the camera's field of view is aligned with the portion of the surface to be imaged.

Preferably, means for illuminating the substrate is provided to enable the camera to image the substrate. Means for illuminating the substrate may comprise one or more light sources. The light source should be positioned relative to the camera such that the camera can image the desired qualities of the features such as size, shape, and position. Lighting can be directed to the surface of the substrate in a downward, upward, or lateral manner. Light may illuminate the surface of the substrate from the back of the substrate in which case the substrate must be optically transparent for the light to be transmitted therethrough. Glass, polycarbonate and other transparent materials are suitable as substrate materials if lighting is provided from the back for the substrate.

To insure that the camera is positioned to image a portion of the surface on which a feature should have been deposited, the camera and inkjet printhead are preferably situated in a manner such that an induced movement of the printhead relative to the substrate results in a corresponding movement of the camera relative to the substrate. This can be achieved through levers, pulleys, gears, a combination thereof, or other mechanical means known to one of ordinary skill in the art such that there is a one-to-one correspondence between the direction and the distance of the induced and corresponding movements. The preferred version of the corresponding movement is substantially identical in direction and distance to the induced movement of the printhead. As shown in FIG. 3, the camera 50 and the printhead 10 are mounted on the same rigid member 70 thus assuring that whenever movement is induced in the printhead 10, the camera 50 is also moved in a substantially identical manner. The printhead 10 is mounted such that the path of droplets as they are dispensed is perpendicular to the surface 21 of the substrate 20. The camera 50 is also mounted perpendicularly to the surface 21 of the substrate 20.

In operation, the printhead controller 110 moves the printhead 10 in a patternwise manner over the surface 21 of the substrate such that the printhead 10, during its movement, passes over the nominal position of every feature to be deposited. The pattern shown in FIG. 3 is a plurality of circular features 22 of diameter D in a straight line wherein the distance between the center of a feature to the center of its nearest neighboring feature is 3D. Thus, the shortest distance between each feature is 2D. When the dispensing orifice 15 of the printhead 10 is directly over the location on the surface 21 of the substrate 20 where a feature 22 is desired, the printhead controller 110 activates the printhead 10 to deposit a droplet of fluid.

As shown in FIG. 3, the camera 50 is mounted behind the printhead 10 such that the camera 50 follows the printhead as the printhead controller 110 positions and activates the printhead. Thus, the camera also passes over substantially the same portion of the substrate surface 21 where the features 22 are supposed to be deposited. Due to the small size and the large number of features, the preferred printhead controller 110 is computerized. In this embodiment of the invention, one or more channels of the printhead controller 110 can serve as the camera controller 150. If the camera controller activates the camera 50 only when the camera is positioned to detect at least a portion of the surface 21 on which a feature should have been deposited, the amount of image data corresponding to areas where features should not have been deposited is generally minimized. The position of the printhead 10 relative to the camera 50, as shown in FIG. 3, results in a lag time between when the printhead 10 passes over a position on which a feature 22 should be deposited and when the camera 50 passes over the position. Thus, the camera controller 150 should be programmed to activate only after a lag time or after the printhead 10 has traveled the distance between the camera 50 and the dispensing orifice 15 of the printhead 10. The programming can be performed by instructing the controller regarding the distance between the camera and the dispensing orifice and/or by manipulation of the image or data file. Alternatively, the camera can be positioned at an angle or optics can be employed such that the camera is capable of acquiring an image of the area on which a feature should be deposited while the feature is being deposited.

FIG. 3 also show a digital line scan camera comprising a plurality of pixels 51. Each pixel is a charge couple device (CCD) in which light or photons are converted into electrons. The number of electrons generated by each pixel depends on the light intensity, spectrum, and time of exposure. When the pixels are arranged in an array, it is possible to convert the signals resulting from an image of light incident on the array to form a representation of the image. However, line scan cameras comprise only a line, not an array, of pixels for line scanning. As shown, the line of pixels 51 of the line scan camera is perpendicular to the plane of FIG. 3. Thus, a line scan camera can be used to image in a two-dimensional manner by moving the camera across an object in a perpendicular direction with respect to the line of pixels, activating the pixels to acquire successive narrow-stripped portions of the image, and combining the successive portions to build a complete two-dimensional image. In order for the camera to image features at the rate features are typically deposited by current inkjet printhead technology, the net data acquisition rate is about 20 to about 60 megabytes per second. Thus, the camera should be capable of acquiring data at a peak rate of at least about 20 megabytes of data per second.

A line scan camera is timed by image and line triggers. When an image trigger is activated, the camera begins to operate. The image trigger allows the line scan camera to acquire a set number of lines. The camera acquires a line of an image when the line trigger is activated. In other words, the image trigger "unlocks" the camera, and the camera acquires a set number of lines if the line trigger is activated the set number of times. Every time the line trigger is activated, each pixel of the line discharges its electrons. Each pixel's discharge translates to a portion of the acquired image.

A preferred version of the present invention uses a digital line camera rather than an array sensor due to the simplicity of the geometry of the line camera. The simplicity of geometry provides ease for determining a sequence of camera activation to avoid duplicative imaging of the same portion of the surface. The length of the field of view of the line scan camera is preferably at least than the diameter of the features. As the camera 50 passes over the features, the camera is activated to image only when the camera is directly over a nominal feature position. Otherwise, the camera neither acquires images nor generates signals. The camera controller 150 controls the image and line triggers of the camera 50 with reference to signals provided by the selected channels of the position encoder which is controlled by a data file. For a line of circular features shown in FIG. 3, activation of the camera in this manner reduces the amount of acquired image data by roughly two-thirds. If the length of the line scan camera is equal to the diameter of each circular feature, for each feature 22 with a diameter D, image acquired for each feature by as shown in FIG. 3 should correspond to a square having sides with a length of D.

As the desired number of features increases, the inkjet printhead may be designed to deposit more than one feature at a time. For example, a printhead may have a plurality of dispensing orifices in a row, each dispensing orifice located at a distance of 3D from its nearest neighboring orifice. The printhead is adapted to deposit features having a diameter D on a surface of a substrate. The printhead is passed over the substrate such that the direction of printhead is perpendicular to the row of orifices. Rows of features are deposited to form an array as shown in FIG. 2 such that the center of each feature 22 located at a distance of 3D to the center of each nearest neighboring feature. A line scan camera, having a line of pixels whose length is slightly larger than the line of dispensing orifices of the printhead, is mounted to follow the printhead such that the line camera pixels are parallel with the rows of features. Again, as the camera passes over the features, the camera is activated to acquire an image only when the camera is directly over a portion of the substrate on which a feature should have deposited. Otherwise, the camera neither acquires an image nor generates a signal. In this instance, however, certain pixels of the line scan camera will never pass over a nominal position of a feature. Thus, decimation of the image to reduce the amount of total image data can be achieved by two different methods. The first is to inactivate the pixels that will not pass over the nominal position of a feature. The second is to eliminate the data from those pixels after scanning. In other words, data corresponding to the rectangle between a column of feature where the column having a width of 2D and the length of the print path in FIG. 2 is eliminated. Thus, both memory and processing resources are conserved.

In another embodiment, a means is provided for comparing an image acquired by the camera with a predetermined standard to produce a signal. Once an image of the nominal area on the surface of the substrate is obtained, the image is compared with that of a predetermined standard. If the image deviates from the predetermined standard, a signal is produced. The signal can be used to alert an operator of the fluid deposition device to out-of-specification features, or to stop the deposition process. If means are provided to convey the signal to the printhead controller, the signal may be adapted to continuously adjust deposition parameters to ensure conformance of features to the predetermined standard. In essence, this embodiment of the invention provides a quality control over features in array fabrication by continuously monitoring and adjusting the fabrication process.

While the present invention can be adapted for use in inspecting patterns where the number of features is relatively small, the invention is particularly useful where the number of features in the pattern is large. There is greater difficulty in handling the amount of imaging data needed to inspect the deposition of a large number of features. With only a few features in the pattern, the need for image data reduction is lessened because current technology is capable of handling the imaging data for a low number of features with only slight difficulty. Thus, it is preferred that the plurality of features comprise at least 1,000 features and more preferably at least 100,000 features.

Currently, there is a need to deposit and inspect fluids containing a variety of composition to form features in array. The compositions may be organic or inorganic. Of particular need is to deposit and inspect biomolecular arrays. Examples of biomolecules include, but are not limited to, oligopeptides, polypeptides, oligonucleotides and polynucleotides. Generally, inkjet technology allows biomolecular arrays to be formed relatively quickly. The peak data acquisition rate of a digital camera needed to keep up with a typical biomolecular array fabrication process is on the order of 60 megabytes per second.

While the preferred embodiment of the present invention provides for the inspection of an array while the array is being deposited, it is sometimes not possible to inspect an array of features while the array is being deposited. Thus, another embodiment of the invention involves an apparatus for inspecting a plurality of features after feature deposition is complete. The apparatus comprises a camera capable of imaging of the surface of the substrate and a controller for positioning and activating the camera to acquire images corresponding to substantially only the portion of the surface on which the features have been deposited. Preferably, the controller is computerized. The many readily available ways to implement a computerized controller are apparent to one of ordinary skill in the art. The technical requirements and preferences for the camera and other elements of the invention are the same as those described above for the preferred embodiment.

Once the pattern has been formed and inspected, the pattern can be exposed to a sample to be tested and then interrogated. The sample can be obtained from a remote location. In addition, interrogation may yield a result or conclusion based on the result that can be transmitted to a remote location. In other words, it is envisioned that as a part of the present invention, the formation and the inspection of the pattern does not have to occur at the same location as the testing and the interrogation of the pattern.

Variations of the present invention will be apparent to those knowledgeable in the art of deposition and inspection of chemical and biological fluids. For example, the printhead is neither limited to depositing circular features nor being oriented in any particular direction with respect to the substrate. In addition, magnification means may be employed to ensure adequate resolution of the features.

It is to be understood that while the invention has been described in conjunction with the preferred specific embodiments thereof, that the foregoing description is intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

What is claimed is:

1. An apparatus for producing and inspecting a plurality of features in a pattern on a surface of a substrate, comprising:

a printhead that deposits a fluid to form a plurality of features in a pattern on a first portion of a substrate surface, leaving a second intervening portion of the substrate surface nominally featureless;

an image acquisition system that images the substrate surface, said image acquisition system comprising:

a camera and a camera controller that positions and activates said camera to image in a two-dimensional manner by moving the camera across said first portion in a perpendicular direction with respect to a line of said features to acquire images corresponding to said first portion and less than all of said second portion; and a printhead controller that positions the printhead relative to the substrate surface and activates the printhead to sequentially deposit the plurality of features in the pattern.

2. The apparatus of claim 1 wherein activation of the printhead by the printhead controller is accompanied by corresponding imaging by the image acquisition system.

3. The apparatus of claim 1 wherein an induced movement of the printhead relative to the substrate results in a corresponding movement of the image acquisition system relative to the substrate.

4. The apparatus of claim 3 wherein the corresponding movement is substantially identical in direction and distance to the induced movement of the printhead.

5. The apparatus of claim 2 wherein the printhead controller is computerized.

6. The apparatus of claim 1 wherein the image acquisition system comprises a digital camera.

7. The apparatus of claim 6 wherein the camera is a line scan camera.

8. The apparatus of claim 6 wherein the camera acquires data at a peak rate of at least about 20 megabytes of data per second.

9. The apparatus of claim 5 wherein the printhead controller functions as said camera controller.

10. The apparatus of claim 7 wherein the line scan camera comprises a line of pixels activated according to a data file.

11. The apparatus of claim 1 further comprising means for illuminating the substrate surface.

12. The apparatus of claim 6 further comprising means for comparing an image acquired by the camera with a predetermined standard to produce a signal.

13. The apparatus of claim 12 further comprising means for conveying the signal to the printhead controller to alter the positioning and activating of the printhead.

14. The apparatus of claim 1 wherein the substrate is transparent.

15. The apparatus of claim 1 wherein the fluid comprises a biomolecule.

16. The apparatus of claim 1 wherein the fluid comprises an oligonucleotide, polynucleotide, oligopeptide, or polypeptide.

17. The apparatus of claim 1 wherein the printhead is an inkjet printhead.

18. The apparatus of claim 1 wherein the pattern is an array.

19. The apparatus of claim 1 wherein the plurality comprises at least 1,000 features.

20. The apparatus of claim 19 wherein the plurality comprises at least 100,000 features.

21. The apparatus of claim 1 wherein said camera controller activates said camera to acquire images corresponding to said first portion and no more than about fifty percent of the second portion of the surface.

22. The apparatus of claim 21 wherein said camera controller activates said camera to acquire images corresponding to said first portion and no more than about twenty-five percent of the second portion of the surface.

23. The apparatus of claim 22 wherein said camera controller activates said camera to acquire images corresponding to said first portion and no more than about ten percent of the second portion of the surface.

24. An apparatus for producing and inspecting a plurality of features in a pattern on a surface of a substrate, said apparatus comprising:
- a printhead that deposits a fluid to form a plurality of features in a pattern on a first portion of a substrate surface, leaving a second intervening portion of the substrate surface nominally featureless;
- an image acquisition system that images the substrate surface, said image acquisition system comprising:
  - a camera and
  - a camera controller comprising hardware and/or software that activates said camera, when said camera is positioned to detect a portion of the substrate surface on which a feature should have been deposited, to image in a two-dimensional manner by moving the camera across said first portion in a perpendicular direction with respect to a line of said features to acquire images corresponding to said first portion and less than all of said second portion; and
- a printhead controller that positions the printhead relative to the substrate surface and activates the printhead to sequentially deposit the plurality of features in the pattern.

25. An apparatus for producing and inspecting an array of nucleic acid features on a surface of a substrate, said apparatus comprising:
- a printhead that deposits a fluid to form an array of nucleic acid features on a first portion of a substrate surface, leaving a second intervening portion of the substrate surface nominally featureless;
- an image acquisition system that images the substrate surface, said image acquisition system comprising:
  - a line scan camera comprising a line of pixels and
  - a camera controller that positions and activates said camera to image in a two-dimensional manner by moving the camera across said first portion in a perpendicular direction with respect to the line of pixels to acquire images corresponding to said first portion and less than all of said second portion; and
- a printhead controller that positions the printhead relative to the substrate surface and activates the printhead to sequentially deposit the fluid to form said array of nucleic acid features on the substrate surface.

* * * * *